(12) United States Patent
Brodjonegoro et al.

(10) Patent No.: US 12,362,043 B2
(45) Date of Patent: Jul. 15, 2025

(54) SYSTEM FOR OPTIMIZING DURATION TIME OF HIGH-PRESSURE LEACHING OF LATERITE NICKEL ORE

(71) Applicants: PT ESG NEW ENERGY MATERIAL, Dki Jakarta (ID); PT QMB NEW ENERGY MATERIALS, Dki Jakarta (ID); GEM CO., LTD., Guangdong (CN); PT GEM INDONESIA NEW ENERGY MATERIALS, Dki Jakarta (ID)

(72) Inventors: Satryo Soemantri Brodjonegoro, Dki Jakarta (ID); Kaihua Xu, Guangdong (CN); Yaning Wang, Dki Jakarta (ID); Rizky Wanaldi, Dki Jakarta (ID); Tegar Mukti Aji, Dki Jakarta (ID); Aad Alief Rasyidi Baking, Dki Jakarta (ID); Andi Syaputra Hasibuan, Dki Jakarta (ID); Piyan Rahmadi, Dki Jakarta (ID)

(73) Assignees: PT ESG NEW ENERGY MATERIAL, Jakarta Selatan (ID); PT QMB NEW ENERGY MATERIALS, Jakarta Selatan (ID); GEM CO., LTD., Shenzhen (CN); PT GEM INDONESIA NEW ENERGY MATERIALS, Jakarta Selatan (ID)

( * ) Notice: Subject to any disclaimer, the term of this patent is extended or adjusted under 35 U.S.C. 154(b) by 0 days.

(21) Appl. No.: 18/870,458

(22) PCT Filed: Jul. 27, 2023

(86) PCT No.: PCT/CN2023/109607
§ 371 (c)(1),
(2) Date: Nov. 29, 2024

(87) PCT Pub. No.: WO2025/020175
PCT Pub. Date: Jan. 30, 2025

(65) Prior Publication Data
US 2025/0166738 A1    May 22, 2025

(51) Int. Cl.
G16C 20/10     (2019.01)
C22B 3/00      (2006.01)

(52) U.S. Cl.
CPC ........... *G16C 20/10* (2019.02); *C22B 23/043* (2013.01)

(58) Field of Classification Search
CPC .............................. G16C 20/10; C22B 23/043
See application file for complete search history.

(56) References Cited

U.S. PATENT DOCUMENTS

2023/0077051 A1    3/2023   Yopps et al.

FOREIGN PATENT DOCUMENTS

| CN | 102002382 A | 4/2011 |
|---|---|---|
| CN | 102681496 A | 9/2012 |

(Continued)

OTHER PUBLICATIONS

International Search Report issued in corresponding International application No. PCT/CN2023/109607, mailed Apr. 8, 2024 (8 pages).

(Continued)

*Primary Examiner* — James A Fiorito

(57) ABSTRACT

A system for optimizing duration time of high-pressure leaching of laterite nickel ore, includes a data collecting module, an actual duration time calculating module configured to obtain an actual duration time of the pulp in the autoclave during the high-pressure leaching process, an optimal duration time determining module configured to obtain an optimal duration time corresponding to a maximum income value, according to the qualities of the pulp, and a duration time control module configured to compare (Continued)

an actual duration time with the optimal duration time under this condition, and control opening degrees of a feed valve and a discharge valve of the autoclave by using a feedback control system, to ensure the actual duration time of the pulp in the autoclave is within the optimal duration time all the time.

11 Claims, 5 Drawing Sheets

(56) References Cited

FOREIGN PATENT DOCUMENTS

| CN | 104263924 A | 1/2015 |
|----|-------------|--------|
| CN | 106086426 A | 11/2016 |
| CN | 107881342 A | 4/2018 |

OTHER PUBLICATIONS

Written Opinion of the International Search Authority in corresponding International application No. PCT/CN2023/109607, mailed Apr. 3, 2024 (6 pages).
Shuyan Yin et al., Experimental Study on Sulfide Precipitation of Nickel Ore Leaching Solution from Red Soil, World Nonferrous Metals, Issue 10, ISSN: 1002-5065, mailed Oct. 15, 2014 (4 pages).

SYSTEM FOR OPTIMIZING DURATION TIME OF HIGH-PRESSURE LEACHING OF LATERITE NICKEL ORE

FIELD OF THE DISCLOSURE

The disclosure relates to the technical field of high-pressure leaching of laterite nickel ore, and in particular to a system for optimizing duration time of high-pressure leaching of laterite nickel ore.

BACKGROUND

The hydrometallurgical process, due to its environmental advantages, is increasingly being widely used in the metallurgical field to replace the pyrometallurgical process. The hydrometallurgical process mainly includes a normal pressure leaching and a pressurized leaching. The pressurized leaching process generally includes firstly making an ore into a pulp, then preheating the pulp, acid leaching the preheated pulp in a high-pressure autoclave, and then lowering a temperature and pressure of the pulp, neutralizing and separating the pulp, and purifying leaching solution.

In the typical pressurized leaching process, before entering the autoclave, a large quantity of steam is required to preheat the pulp to a specified temperature, and a large quantity of heated steam needs to be consumed. Heat utilization efficiency is low, heating time is long, and heating costs are high. On the other hand, the leaching solution leached at a high temperature and a high pressure needs to be gradually lowered to a low temperature and a normal pressure by using a flash tank. In this process, a large quantity of flash steam is generated. This part of steam may be used to mix and preheat the ore pulp to make full use of residual heat, and reduce steam consumption and operating costs.

The leaching time of high-pressure leaching process plays an important role in the effect of high-pressure acid leaching. Too short acid leaching time may lead to incomplete leaching, low metal leaching rate and low ore utilization rate. Excessive acid leaching time can lead to lower production efficiency, lower pulp processing per unit time, and lower output per unit time. Therefore, how to determine an optimal duration time of the high-pressure leaching process of laterite nickel ore and how to control a system under an operation condition of the optimal duration time plays a vital role in efficient operation of laterite nickel ore hydrometallurgical processing system.

However, the optimal leaching time in the high-pressure leaching process is dynamically changed, and is affected by various factors such as a leaching temperature, a feed ore component, a feed amount, and an operating condition of a preheating-flash system. Because the actual leaching time calculation and optimization process of high-pressure leaching process is relatively complicated, there is no relevant research and technical report on the duration time optimization of high-pressure leaching of laterite nickel ore.

The optimization time is currently determined mainly by using a laboratory small test experiment. However, because there is a difference between a mass transfer and heat transfer process between a small test apparatus and a large autoclave, the optimal duration time determined by the small test apparatus is different from the optimal duration time in the large autoclave, and an optimal duration time under an operating condition of the large autoclave cannot be completely deduced by using experimental data of the small test apparatus. Due to the complexity of calculation and optimization process of duration time in large-scale autoclave, there is no relevant research and technical report on duration time optimization of high-pressure leaching of laterite nickel ore.

SUMMARY

The purpose of this disclosure is to provide a system for optimizing duration time of high-pressure leaching of laterite nickel ore to determine the actual duration time and the optimal duration time of the pulp in the high-pressure leaching process, and adjust the duration time of the high-pressure leaching of laterite nickel according to production fluctuation to ensure the high-pressure leaching process is performed in the optimal dynamic state all the time.

In order to solve the above technical problems, this disclosure provides a system for optimizing duration time of high-pressure leaching of laterite nickel ore, comprising: a data collecting module, an actual duration time calculating module, an optimal duration time determining module, and a duration time control module, wherein the data collecting module is configured to collect qualities of pulp, sulfuric acid, and steam that enter an autoclave within a unit time during a high-pressure leaching process, outlet temperatures of a high-temperature preheating tower, a medium-temperature preheating tower, a low-temperature preheating tower, a high-temperature flash tank, a medium-temperature flash tank, and a low-temperature flash tank, a leaching temperature of the autoclave, a composition of the pulp that enters the autoclave within the unit time, and prices of nickel, sulfuric acid, and steam that enter the autoclave;

the actual duration time calculating module is configured to obtain an actual duration time of the pulp in the autoclave during the high-pressure leaching process, according to the qualities of the pulp, the sulfuric acid, and the steam that enter the autoclave within the unit time during the high-pressure leaching process, the actual duration time of the pulp in the autoclave during the high-pressure leaching process, the outlet temperatures of the high-temperature preheating tower, the mediate-temperature preheating tower, the low-temperature preheating tower, the high-temperature flashing tank, the mediate-temperature flashing tank, and the low-temperature flashing tank, and the leaching temperature in the autoclave;

the optimal duration time determining module is configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the mediate-temperature preheating tower, the low-temperature preheating tower, the high-temperature flashing tank, the mediate-temperature flashing tank, the leaching temperature in the autoclave, a composition of the pulp that enters the autoclave within the unit time, and the prices of nickel, sulfuric acid, and steam that enter the autoclave; and the duration time control module is configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time.

In some embodiments, a specific method of the actual duration time calculating module configured to obtain an actual duration time of the pulp in the autoclave during the high-pressure leaching process, according to the qualities of the pulp, the sulfuric acid, and the steam that enter the autoclave within the unit time during the high-pressure leaching process, the actual duration time of the pulp in the autoclave during the high-pressure leaching process, the outlet temperatures of the high-temperature preheating tower, the mediate-temperature preheating tower, the low-temperature preheating tower, the high-temperature flashing tank, the mediate-temperature flashing tank, and the low-temperature flashing tank, and the leaching temperature in the autoclave, comprises:

obtaining a total feed quantity in the current unit time;
obtaining an effective volume of the autoclave;
obtaining a liquid density at the current leaching temperature, according to the leaching temperature in the autoclave; and
obtaining the actual duration time of the pulp in the autoclave, according to the effective volume of the autoclave, the total feed amount in the unit time, and the liquid density at the current leaching temperature.

In some embodiments, a specific method of obtaining a total feed quantity in the current unit time, comprises:

obtaining the qualities of pulp, sulfuric acid and steam that enter the autoclave within the unit time;
obtaining a quality of steam that condenses into the pulp during steam heating in the preheating tower within the unit time, according to the outlet temperatures of the high-temperature preheating tower, the middle-temperature preheating tower, the low-temperature preheating tower, the high-temperature flash tank, the middle-temperature flash tank, and the low-temperature flash tank; and
obtaining a total feed quantity within the current unit time, according to the qualities of the pulp, the sulfuric acid, and the steam that enter the autoclave within the unit time, and the quality of steam that condenses into the pulp during steam heating in the preheating tower within the unit time.

In some embodiments, a specific calculation formula of obtaining a quality of steam that condenses into the pulp during steam heating in the preheating tower within the unit time, according to the outlet temperatures of the high-temperature preheating tower, the middle-temperature preheating tower, the low-temperature preheating tower, the high-temperature flash tank, the middle-temperature flash tank, and the low-temperature flash tank is as follows:

$$M_{preheating} = \frac{C_p * (T_{hpre} - T_{mpre})}{H_{hflash} - H_{hpreliquid}} + \frac{C_p * (T_{mpre} - T_{lpre})}{H_{mflash} - H_{mpreliquid}} + \frac{C_p * (T_{lpre} - T_{room\ temperature})}{H_{lflash} - H_{lpreliquid}}$$

wherein, $M_{preheating}$ represents the quality of the steam that condenses into the pulp in pre-heating tower during steam heating in the unit time, and $H_{hflash}$, $H_{mflash}$, and $H_{lflash}$ respectively represents vapor enthalpies of the outlet temperatures of the high-temperature flash tank, the medium-temperature flash tank, and the low-temperature flash tank, and are obtained by combining the outlet temperatures of the high-temperature flash tank, the medium-temperature flash tank, and the low-temperature flash tank with database, $H_{hprliquid}$, $H_{mpreliquid}$, and $H_{lpreliquid}$ respectively represents liquid enthalpies of the outlet temperatures of the high-temperature preheating tower, the medium-temperature preheating tower, and the low-temperature preheating tower, and are obtained by combining the outlet temperatures of the high-temperature preheating tower, the medium-temperature preheating tower, and the low-temperature preheating tower with database, $T_{hpre}$, $T_{mpre}$, and $T_{lpre}$ respectively represents the outlet temperatures of the high-temperature preheating tower, the medium-temperature preheating tower, and the low-temperature preheating tower and $C_p$ represents a specific heat capacity of the pulp.

In some embodiments, the specific heat capacity of the pulp is calculated as follow:

$$C_p = 4.2 * (1 - c) + 0.364 * c$$

wherein $C_p$ represents the specific heat capacity of the pulp, c represents a solid content in the pulp, and is obtained by collecting a pulp flow rate and a pulp concentration.

In some embodiments, a specific calculation formula of obtaining a total feed quantity within the current unit time, according to the qualities of the pulp, the sulfuric acid, and the steam that enter the autoclave within the unit time, and the quality of steam that condenses into the pulp during steam heating in the preheating tower within the unit time is as follows:

$$M_{total} = M_{pulp} + M_{H_2SO_4} + M_{autoclave} + M_{preheating}$$

wherein, $M_{total}$ represents the total feed quantity within the current unit time, $M_{pulp}$, $M_{H_2SO_4}$, and $M_{antoclave}$ respectively represents the qualities of the pulp, the sulfuric acid, and the steam that enter the autoclave within the unit time during high-pressure leaching process, and $M_{preheating}$ represents the quality of the steam that condenses into the pulp in pre-heating tower during steam heating in the unit time.

In some embodiments, a specific calculation formula of obtaining a liquid density at the current leaching temperature, according to the leaching temperature in the autoclave is as follows:

$$\rho_T = 15.81747 + 9.87802 * T - 0.035239T^2 + 5.38051 * 10^{-5}T^3 - 3.2612 * 10^{-8}T^4$$

wherein $\rho_T$ represents the liquid density at the current leaching temperature, and T represents the current leaching temperature.

In some embodiments, a specific calculation formula of obtaining the actual duration time of the pulp in the autoclave, according to the effective volume of the autoclave, the total feed amount in the unit time, and the liquid density at the current leaching temperature is as follows:

$$t_{act} = \frac{V}{W_T}$$

$$W_T = \frac{M_{total}}{\rho_T}$$

wherein, $t_{act}$ represents the actual duration time of the pulp in the autoclave, V represents the effective volume of the autoclave, $W_T$ represents a total feed flow rate, $M_{total}$ represents the total feed quantity within the current unit time, and $\rho_T$ represents the liquid density at the current leaching temperature.

In some embodiments, a specific method of the optimal duration time determining module configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the mediate-temperature preheating tower, the low-temperature preheating tower, the high-temperature flashing tank, the mediate-temperature flashing tank, the leaching temperature in the autoclave, a composition of the pulp that enters the autoclave within the unit time, and the prices of nickel, sulfuric acid, and steam that enter the autoclave, comprises:

setting different duration times in sequence;
calculating each income value of each duration time; and
comparing the income value at each duration time to obtain a duration time corresponding to the maximum income value as the optimal duration time, and outputting the optimal duration time.

In some embodiments, a specific calculation formula of calculating each income value of each duration time is as follows:

$$incomevalue = \\ (M_{pulp} \times c_{Ni} \times X_{Ni} \times P_{Ni} - M_{H_2SO_4} P_{H_2SO_4} - M_{autoclave} P_{steam}) \times \frac{24\,h}{t}$$

$$3.12 \times 10^7 \times e^{-\frac{87.75 \times 10^3}{RT}} \frac{M_{H_2SO_4}}{W_T} t = 1 - 3(1 - X_{Ni})^{\frac{2}{3}} + 2(1 - X_{Ni})$$

wherein, $P_{Ni}$, $P_{H_2SO_4}$, and $P_{steam}$, respectively represent the prices of metal nickel, sulfuric acid, and steam in the unit mass, $c_{Ni}$ represents a content of Ni in the pulp, $M_{pulp}$, $M_{H_2SO_4}$, and $M_{autoclave}$ respectively represent the qualities of the pulp, the sulfuric acid, and the steam that enter the autoclave within the unit time during the high-pressure leaching process, $X_{Ni}$ represents a conversion rate of Ni in the pulp, h represents an hour, T represents the current leaching temperature, $M_{H_2SO_4}$ represents a quality of sulfuric acid entering the autoclave in the unit time during the high-pressure leaching process, $W_T$ represents a total feed flow rate, t represents the current set duration time, and R represents a gas constant.

In some embodiments, a specific method of the duration time control module configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time, comprises:

if the current actual duration time is less than the optimal duration time, reduce the opening of the feed valve and/or the discharge valve of the autoclave; and
if the current actual duration time is greater than the optimal duration time, increase the opening of the feed valve and/or the discharge valve of the high-pressure.

Compared with existing technologies, the beneficial effect of this disclosure is: the actual duration time and the optimal duration time are obtained by inputting an operation condition such as the real-time incoming ore composition, the leaching temperature, and the acid-to-ore ratio into a calculation model. Thus, the duration time of a high-pressure leaching link of laterite nickel ore can be adjusted according to production fluctuation, and the high-pressure leaching process is always performed in a dynamic optimal state of the optimal duration time. Compared with the typical method for optimizing the duration time by the small test, the method has advantages of fast response and optimized precision.

BRIEF DESCRIPTION OF THE DRAWINGS

Accompanying drawings are for providing further understanding of embodiments of the disclosure. The drawings form a part of the disclosure and are for illustrating the principle of the embodiments of the disclosure along with the literal description. Apparently, the drawings in the description below are merely some embodiments of the disclosure, a person skilled in the art can obtain other drawings according to these drawings without creative efforts. In the figures.

DETAILED DESCRIPTION OF PREFERRED EMBODIMENTS

The technical solutions in the embodiments of the application will be described clearly and completely in combination with the drawings in the embodiments of this disclosure.

Figure 1:
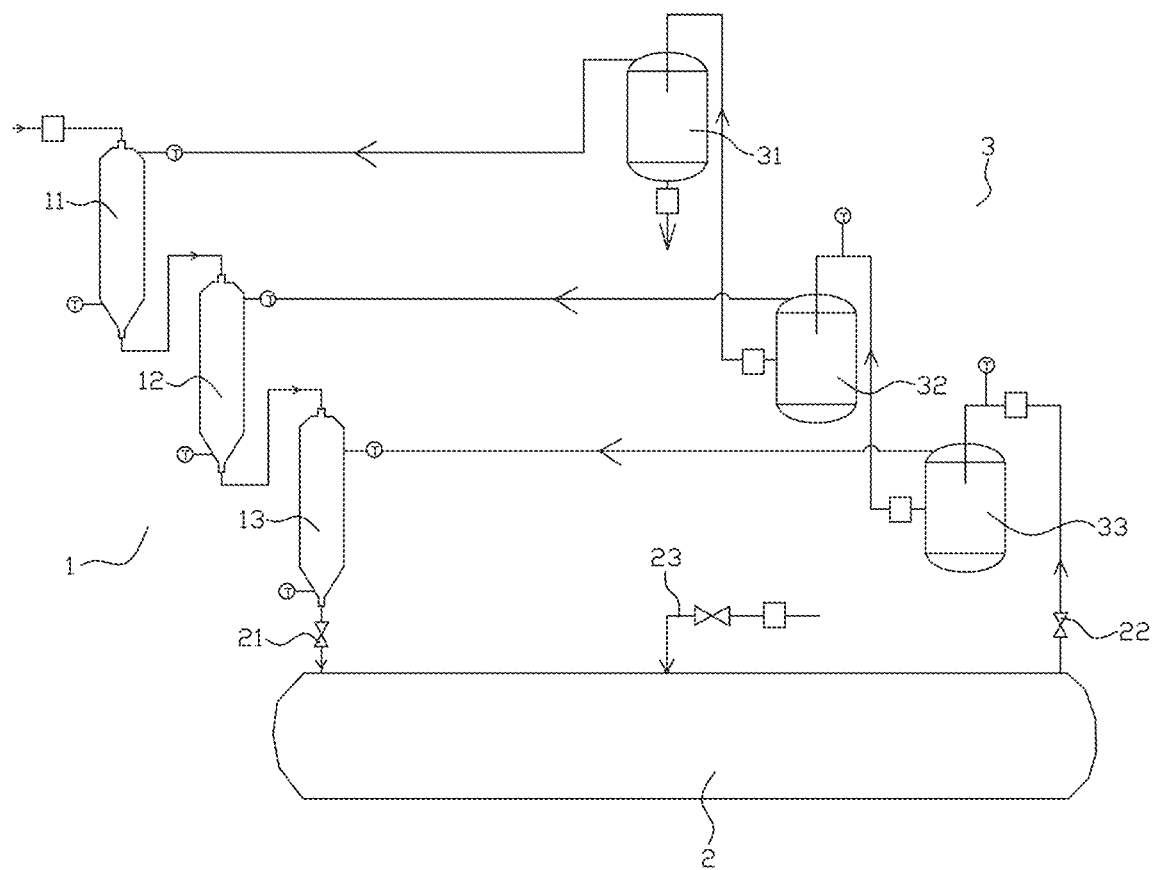
FIG. 1 is a schematic view of a system for optimizing duration time of high-pressure leaching of laterite nickel ore, according to an embodiment of the disclosure.

Referring to FIG. 1, to facilitate understanding of the disclosure, a structure of a typical high-temperature leaching system of laterite nickel ore is firstly described.

The typical high-temperature leaching system of laterite nickel ore includes a preheating mechanism 1, an autoclave 2, and a flash mechanism 3.

The preheating mechanism 1 includes a plurality of low-temperature preheating tower 11, medium-temperature preheating tower 12, and high-temperature preheating tower 13 connected in series. Wherein, a first dielectric inlet of the low-temperature preheating tower 11 is configured to access a pulp. First dielectric inlets of the medium-temperature preheating towers 12 and the high-temperature preheating tower 13 are connected to an outlet of the previous preheating tower.

A material inlet of the autoclave 2 is connected to an outlet of the high-temperature preheating tower 13. The material inlet of the autoclave 2 is provided with a feed valve 21. A material outlet of the autoclave 2 is provided with a discharge valve 22. A steam input pipe 23 is further disposed in the autoclave 2 to access steam.

The flash mechanism 3 includes a low-temperature flash tank 31, a medium-temperature flash tank 32, and a high-temperature flash tank 33 connected in series. Wherein, each of the flash tanks 33 is corresponding to each of the preheaters. A material inlet of the high-temperature flash tank 33 is connected to the material outlet of the high-pressure kettle 2. A material inlet of the medium-temperature flash tank 32 is connected to the material outlet of the high-temperature flash tank 33. A material inlet of the low-temperature flash tank 31 is connected to the material outlet of the medium-temperature flash tank 32. A steam outlet of each flash tank is connected to a corresponding second medium inlet of the preheater.

Figure 2:
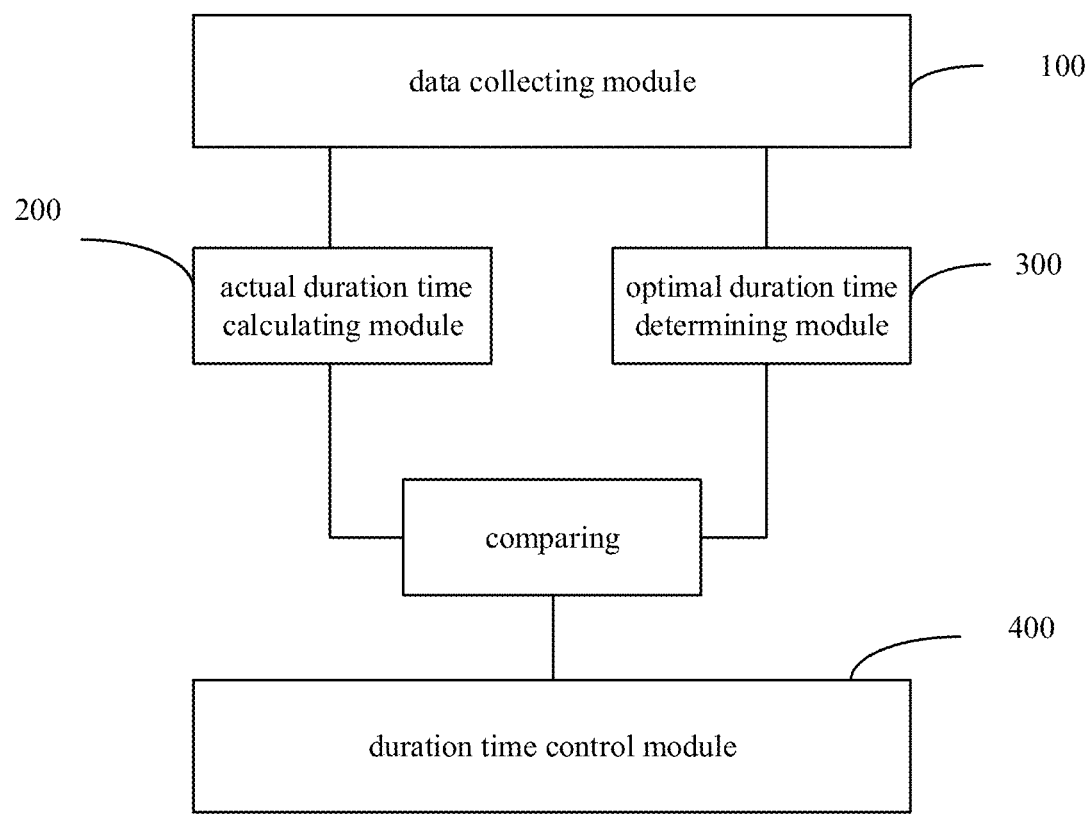
FIG. 2 is a block diagram of the system for optimizing duration time of high-pressure leaching of laterite nickel ore, according to an embodiment of the disclosure.

Referring to FIG. 2, the disclosure provides a duration time optimization system for high-pressure leaching of laterite nickel ore, including a data collecting module 100, an actual duration time calculating module 200, an optimal duration time determining module 300, and a duration time control module 400.

The data collecting module 100 is configured to collect qualities of pulp, sulfuric acid, and steam that enter an autoclave within a unit time during a high-pressure leaching process, outlet temperatures of a high-temperature preheating tower, a medium-temperature preheating tower, a low-temperature preheating tower, a high-temperature flash tank, a medium-temperature flash tank, and a low-temperature flash tank, a leaching temperature of the autoclave, a composition of the pulp that enters the autoclave within the unit time, and prices of nickel, sulfuric acid, and steam that enter the autoclave;

The actual duration time calculating module 200 is configured to obtain an actual duration time of the pulp in the autoclave during the high-pressure leaching process, according to the qualities of the pulp, the sulfuric acid, and the steam that enter the autoclave within the unit time during the high-pressure leaching process, the actual duration time of the pulp in the autoclave during the high-pressure leaching process, the outlet temperatures of the high-temperature preheating tower, the mediate-temperature preheating tower, the low-temperature preheating tower, the high-temperature flashing tank, the mediate-temperature flashing tank, and the low-temperature flashing tank, and the leaching temperature in the autoclave; and The optimal duration time determining module 300 is configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the mediate-temperature preheating tower, the low-temperature preheating tower, the high-temperature flashing tank, the mediate-temperature flashing tank, the leaching temperature in the autoclave, a composition of the pulp that enters the autoclave within the unit time, and the prices of nickel, sulfuric acid, and steam that enter the autoclave; and The duration time control module 400 is configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time.

In the technical solution provided in the disclosure, the actual duration time and the optimal duration time are obtained by inputting an operation condition such as the real-time incoming ore composition, the leaching temperature, and the acid-to-ore ratio into a calculation model. Thus, the duration time of a high-pressure leaching link of laterite nickel ore can be adjusted according to production fluctuation, and the high-pressure leaching process is always performed in a dynamic optimal state of the optimal duration time. Compared with the typical method for optimizing the duration time by the small test, the method has advantages of fast response and optimized precision.

Figure 3:
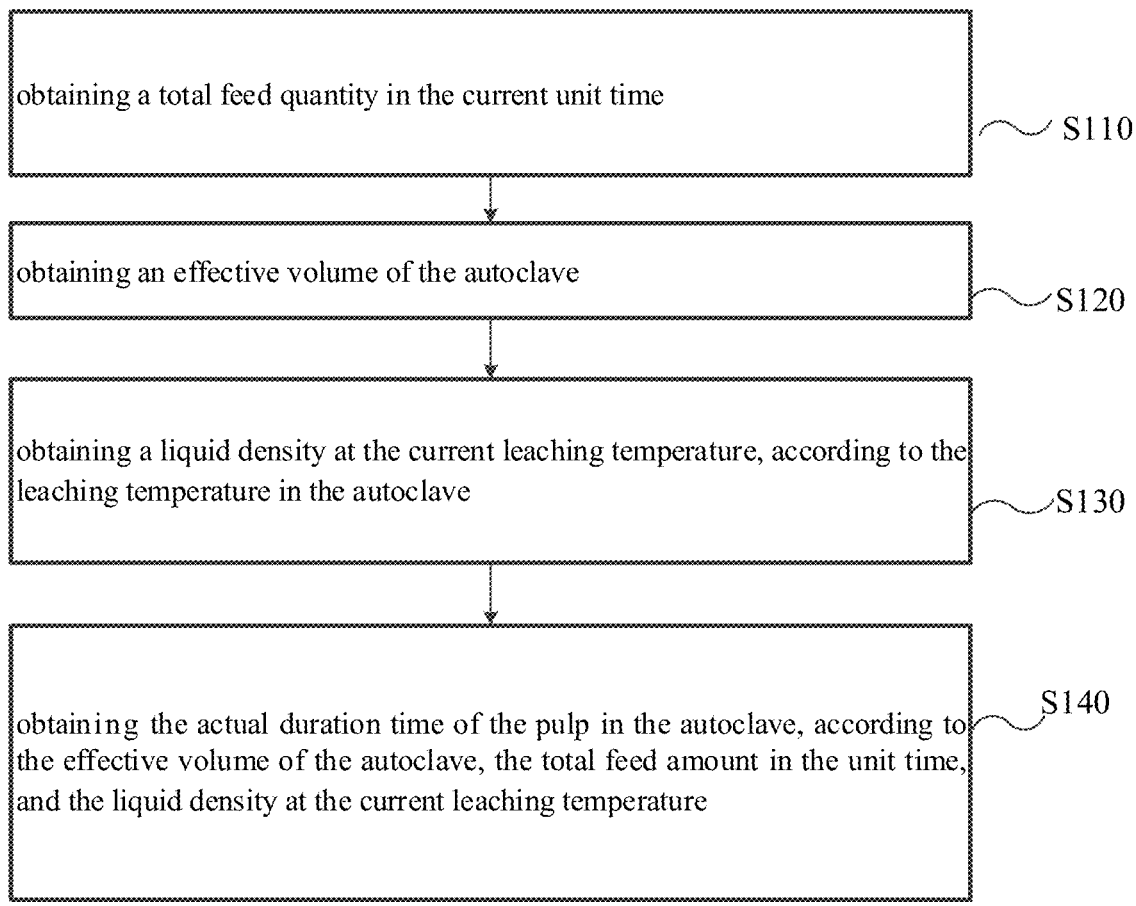
FIG. 3 is a flowchart of a calculating method of an actual duration time calculating module in FIG. 2, according to an embodiment of the disclosure.

To specifically implement a function of the actual duration time calculating module 200, referring to FIG. 3, in a preferred embodiment, the actual duration time calculating module 200 is configured to obtain an actual duration time of the pulp in the autoclave during the high-pressure leaching process, according to the qualities of the pulp, the sulfuric acid, and the steam that enter the autoclave within the unit time during the high-pressure leaching process, the actual duration time of the pulp in the autoclave during the high-pressure leaching process, the outlet temperatures of the high-temperature preheating tower, the mediate-temperature preheating tower, the low-temperature preheating tower, the high-temperature flashing tank, the mediate-temperature flashing tank, and the low-temperature flashing tank, and the leaching temperature in the autoclave, a method thereof includes:

S110. obtaining a total feed quantity in the current unit time.

Figure 4:
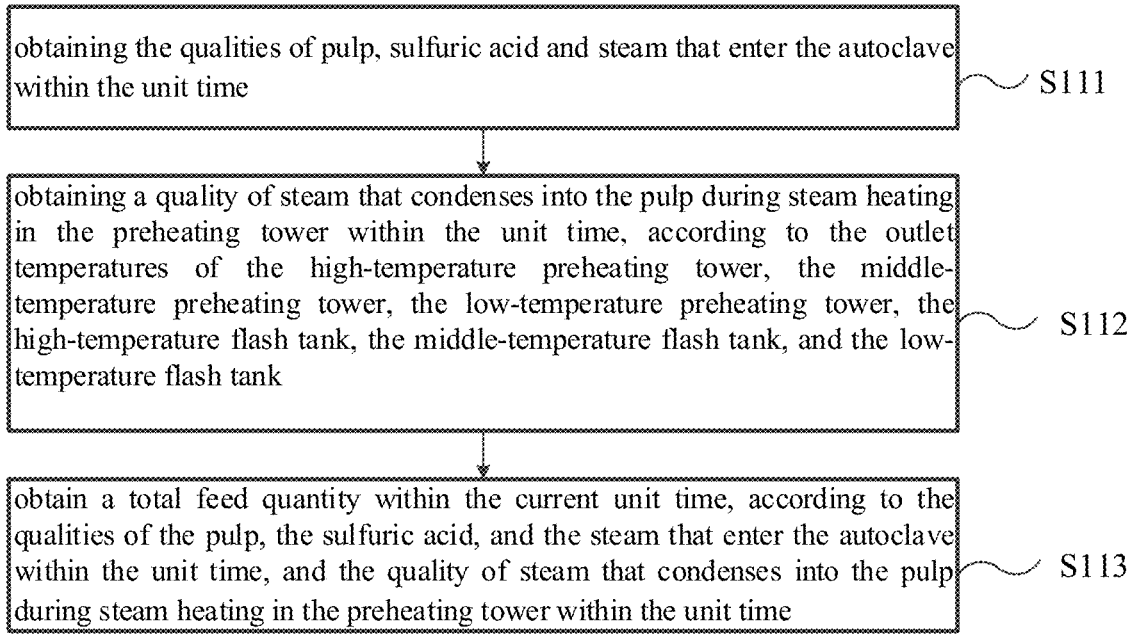
FIG. 4 is a flowchart of step S110 in FIG. 3, according to an embodiment of the disclosure.

Referring to FIG. 4, step S110 specifically includes:

S111. obtaining the qualities of pulp, sulfuric acid and steam that enter the autoclave within the unit time. Because the pulp in the preheating tower condenses into water and the pulp density changes with temperature in a heat exchange process, a flow rate of the feed pulp in the autoclave and an actual pulp volume in the autoclave are fluctuation values, and accurate values can be obtained by means of accurate calculation according to various factors. Therefore, besides obtaining the qualities of the pulp, sulfuric acid, and steam that enter the autoclave within the unit time, the qualities of the condensed pulp in the preheating process in the unit time needs to be obtained.

S112. obtaining a quality of steam that condenses into the pulp during steam heating in the preheating tower within the unit time, according to the outlet temperatures of the high-temperature preheating tower, the middle-temperature preheating tower, the low-temperature preheating tower, the high-temperature flash tank, the middle-temperature flash tank, and the low-temperature flash tank.

A specific calculation formula of step S112 is as follows:

$$M_{preheating} = \frac{C_p * (T_{hpre} - T_{mpre})}{H_{hflash} - H_{hpreliquid}} + \frac{C_p * (T_{mpre} - T_{lpre})}{H_{mflash} - H_{mpreliquid}} + \frac{C_p * (T_{lpre} - T_{room\,temperature})}{H_{lflash} - H_{lpreliquid}}$$

Wherein, $M_{preheating}$ represents the quality of the steam that condenses into the pulp in pre-heating tower during steam heating in the unit time, and $H_{hflash}$, $H_{mflash}$, and $H_{lflash}$ respectively represents vapor enthalpies of the outlet temperatures of the high-temperature flash tank, the medium-temperature flash tank, and the low-temperature flash tank, and are obtained by combining the outlet temperatures of the high-temperature flash tank, the medium-temperature flash tank, and the low-temperature flash tank with database, $H_{hprliquid}$, $H_{mpreliquid}$, and $H_{lpreliquid}$ respectively represents liquid enthalpies of the outlet temperatures of the high-temperature preheating tower, the medium-temperature preheating tower, and the low-temperature preheating tower, and are obtained by combining the outlet temperatures of the high-temperature preheating tower, the medium-temperature preheating tower, and the low-temperature preheating tower with database, $T_{hpre}$, $T_{mpre}$, and $T_{lpre}$ respectively represents the outlet temperatures of the high-temperature preheating tower, the medium-temperature preheating tower, and the low-temperature preheating tower and $C_p$ represents a specific heat capacity of the pulp.

Wherein, a formula for calculating the specific heat capacity of the pulp is as follows:

$$C_p = 4.2*(1-c) + 0.364*c$$

Wherein $C_p$ represents the specific heat capacity of the pulp, c represents a solid content in the pulp, and is obtained by collecting a pulp flow rate and a pulp concentration.

S113. obtaining a total feed quantity within the current unit time, according to the qualities of the pulp, the sulfuric acid, and the steam that enter the autoclave within the unit time, and the quality of steam that condenses into the pulp during steam heating in the preheating tower within the unit time.

A specific calculation formula of step S13 is as follows:

$$M_{total} = M_{pulp} + M_{H_2SO_4} + M_{autoclave} + M_{preheating}$$

wherein, $M_{total}$ represents the total feed quantity within the current unit time, $M_{pulp}$, $M_{H_2SO_4}$, and $M_{antoclave}$ respectively represents the qualities of the pulp, the sulfuric acid, and the steam that enter the autoclave within the unit time during high-pressure leaching process, and $M_{preheating}$ represents the quality of the steam that condenses into the pulp in pre-heating tower during steam heating in the unit time.

S120. obtaining an effective volume of the autoclave.

S130. obtaining a liquid density at the current leaching temperature, according to the leaching temperature in the autoclave.

A specific formula is as follows:

$$\rho_T = 15.81747 + 9.87802*T - 0.035239T^2 + 5.38051*10^{-5}T^3 - 3.2612*10^{-8}T^4$$

Wherein $\rho_T$ represents the liquid density at the current leaching temperature, and T represents the current leaching temperature.

S140. obtaining the actual duration time of the pulp in the autoclave, according to the effective volume of the autoclave, the total feed amount in the unit time, and the liquid density at the current leaching temperature.

A specific calculation formula is as follows:

$$t_{act} = \frac{V}{W_T}$$

$$W_T = \frac{M_{total}}{\rho_T}$$

Wherein, $t_{act}$ represents the actual duration time of the pulp in the autoclave, V represents the effective volume of the autoclave, $W_T$ represents a total feed flow rate, $M_{total}$ represents the total feed quantity within the current unit time, and $\rho_T$ represents the liquid density at the current leaching temperature.

The actual duration time of the pulp in the autoclave may be obtained by the above-mentioned steps.

Figure 5:
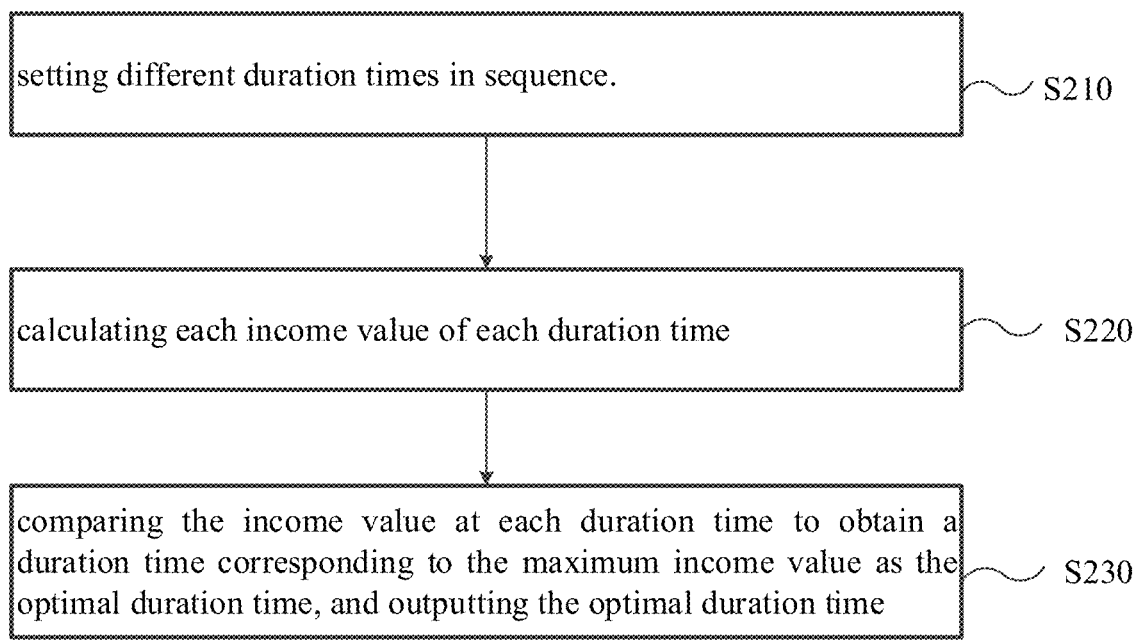
FIG. 5 is a flowchart of a calculating method of an optimal duration time determining module in FIG. 2, according to an embodiment of the disclosure.

To specifically implement a function of the optimal duration time determining module 300, referring to FIG. 5, in a preferred embodiment, the optimal duration time determining module 300 is configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the mediate-temperature preheating tower, the low-temperature preheating tower, the high-temperature flashing tank, the mediate-temperature flashing tank, the leaching temperature in the autoclave, a composition of the pulp that enters the autoclave within the unit time, and the prices of nickel, sulfuric acid, and steam that enter the autoclave, a specific method includes the following steps:

S210. setting different duration times in sequence.

S220. calculating each income value of each duration time.

A specific formula for calculating each income value in each duration time is as follows:

$$incomevalue = (M_{pulp} \times c_{Ni} \times X_{Ni} \times P_{Ni} - M_{H_2SO_4}P_{H_2SO_4} - M_{autoclave}P_{steam}) \times \frac{24h}{t}$$

$$3.12 \times 10^7 \times e^{-\frac{87.75 \times 10^3}{RT}} \frac{M_{H_2SO_4}}{W_T} t = 1 - 3(1-X_{Ni})^{\frac{2}{3}} + 2(1-X_{Ni})$$

wherein, $P_{Ni}$, $P_{H_2SO_4}$, and $P_{steam}$, respectively represent the prices of metal nickel, sulfuric acid, and steam in the unit mass, $c_{Ni}$ represents a content of Ni in the pulp, $M_{pulp}$, $M_{H_2SO_4}$, and $M_{autoclave}$ respectively represent the qualities of the pulp, the sulfuric acid, and the steam that enter the autoclave within the unit time during the high-pressure leaching process, $X_{Ni}$ represents a conversion rate of Ni in the pulp, h represents an hour, T represents the current leaching temperature, $M_{H_2SO_4}$ represents a quality of sulfuric acid entering the autoclave in the unit time during the high-pressure leaching process, $W_T$ represents a total feed flow rate, t represents the current set duration time, and R represents a gas constant.

S230. comparing the income value at each duration time to obtain a duration time corresponding to the maximum income value as the optimal duration time, and outputting the optimal duration time.

The optimal time corresponding to the maximum gain value in the current condition may be obtained by the above-mentioned steps.

To specifically implement a function of the duration time control module 400, referring to FIG. 2, in a preferred embodiment, that the duration time control module 400 is configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time, specifically includes:

If the current actual duration time is less than the optimal duration time, reduce the opening of the feed valve and/or the discharge valve of the autoclave.

If the current actual duration time is greater than the optimal duration time, increase the opening of the feed valve and/or the discharge valve of the high-pressure.

In conclusion, in the technical solution provided in the disclosure, an actual duration time and an optimal duration time are obtained by inputting an operation condition such as a real-time incoming ore composition, an acid leaching temperature, and an acid-to-ore ratio into a calculation model. Thus, a duration time of a high-pressure leaching link of laterite nickel ore can be adjusted according to production fluctuation to ensure a high-pressure leaching process is always in a dynamic optimal state of the optimal duration time. Compared with a conventional method for optimizing a duration time by using a small experiment, the method has advantages of fast response and optimized precision.

To verify the reliability of the technical solution, a set of verification tests is designed. The test conditions are shown in Table 1, and Table 1 shows optimal duration times under conditions in which leaching temperatures are respectively 245° C. and 250° C. and an acid-to-ore ratio is 0.33. For an operating condition of 250° C. and an acid-to-ore ratio of 0.33, the optimal duration time is 50 minutes, which increases the profit per hour by 103$ compared with that before optimization. For an operating condition of 250° C. and an acid-to-ore ratio of 0.33, the optimal duration time is 54 minutes, which increases the profit per hour by 7$ compared with that before optimization. The optimal duration time changes with the set operating conditions such as leaching temperature and acid-to-ore ratio. After optimization, the system can effectively improve the unit time income of the high-pressure leaching process of laterite nickel ore.

| High-pressure leaching temperature | acid-to-ore ratio | Ni leaching rate (%) | Duration time (min) | Feed quantity per unit time (m³/h) | Ni output per unit time (kg/h) | Co leaching rate (%) | Al leaching rate (%) | $/h |
|---|---|---|---|---|---|---|---|---|
| 250° C. | 0.33 | 98 | 55 | 50 | 34.0 | 100 | 31 | 0 |
| | | 98 | 50 | 56 | 38.1 | 100 | 20 | +103 |
| 245° C. | 0.33 | 87 | 50 | 55 | 33.2 | 97 | 60 | 0 |
| | | 91 | 52 | 53 | 33.5 | 98 | 58 | +5.2 |
| | | 93 | 54 | 52 | 33.6 | 99 | 54 | +7.0 |
| | | 96 | 56 | 49 | 32.7 | 100 | 48 | −8.7 |
| | | 98 | 58 | 47 | 32.0 | 100 | 39 | −20.8 |

The above-mentioned descriptions are merely preferred specific implementations of the disclosure, but are not intended to limit the protection scope of the disclosure. Any variation or replacement readily figured out by a person skilled in the art within the technical scope disclosed in the disclosure shall fall within the protection scope of the disclosure.

What is claimed is:

1. A system for optimizing duration time of high-pressure leaching of laterite nickel ore, comprising a data collecting module, an actual duration time calculating module, an optimal duration time determining module, and a duration time control module, wherein the data collecting module is configured to collect qualities of pulp, sulfuric acid, and steam that enter an autoclave within a unit time during a high-pressure leaching process, outlet temperatures of a high-temperature preheating tower, a medium-temperature preheating tower, a low-temperature preheating tower, a high-temperature flash tank, a medium-temperature flash tank, and a low-temperature flash tank, a leaching temperature of the autoclave, a composition of the pulp that enters the autoclave within the unit time, and prices of nickel, sulfuric acid, and steam that enter the autoclave;

the actual duration time calculating module is configured to obtain an actual duration time of the pulp in the autoclave during the high-pressure leaching process, according to the qualities of the pulp, the sulfuric acid, and the steam that enter the autoclave within the unit time during the high-pressure leaching process, the outlet temperatures of the high-temperature preheating tower, the medium-temperature preheating tower, the low-temperature preheating tower, the high-temperature flash tank, the medium-temperature flash tank, and the low-temperature flash tank, and the leaching temperature in the autoclave;

the optimal duration time determining module is configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the medium-temperature preheating tower, the low-temperature preheating tower, the high-temperature flash tank, the medium-temperature flash tank, the low-temperature flash tank, the leaching temperature in the autoclave, the composition of the pulp that enters the autoclave within the unit time, and the prices of nickel, sulfuric acid, and steam that enter the autoclave; and the duration time control module is configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time.

2. The system for optimizing duration time of high-pressure leaching of laterite nickel ore of claim 1, wherein a specific method of the actual duration time calculating module configured to obtain an actual duration time of the pulp in the autoclave during the high-pressure leaching process, according to the qualities of the pulp, the sulfuric acid, and the steam that enter the autoclave within the unit time during the high-pressure leaching process, the outlet temperatures of the high-temperature preheating tower, the medium-temperature preheating tower, the low-temperature preheating tower, the high-temperature flash tank, the medium-temperature flash tank, and the low-temperature flash tank, and the leaching temperature in the autoclave, comprises:
  obtaining a total feed quantity in the current unit time;
  obtaining an effective volume of the autoclave;
  obtaining a liquid density at the current leaching temperature, according to the leaching temperature in the autoclave; and
  obtaining the actual duration time of the pulp in the autoclave, according to the effective volume of the autoclave, the total feed amount in the unit time, and the liquid density at the current leaching temperature.

3. The system for optimizing duration time of high-pressure leaching of laterite nickel ore of claim 2, wherein a specific method of obtaining a total feed quantity in the current unit time, comprises:
  obtaining the qualities of pulp, sulfuric acid and steam that enter the autoclave within the unit time;
  obtaining a quality of steam that condenses into the pulp during steam heating in the preheating tower within the unit time, according to the outlet temperatures of the high-temperature preheating tower, the medium-temperature preheating tower, the low-temperature preheating tower, the high-temperature flash tank, the medium-temperature flash tank, and the low-temperature flash tank; and
  obtaining a total feed quantity within the current unit time, according to the qualities of the pulp, the sulfuric acid, and the steam that enter the autoclave within the unit time, and the quality of steam that condenses into the pulp during steam heating in the preheating tower within the unit time.

4. The system for optimizing duration time of high-pressure leaching of laterite nickel ore of claim 3, wherein a specific calculation formula of obtaining a quality of steam that condenses into the pulp during steam heating in the preheating tower within the unit time, according to the outlet temperatures of the high-temperature preheating tower, the medium-temperature preheating tower, the low-temperature preheating tower, the high-temperature flash tank, the medium-temperature flash tank, and the low-temperature flash tank is as follows:

$$M_{preheating} = \frac{C_p * (T_{hpre} - T_{mpre})}{H_{hflash} - H_{hpreliquid}} + \frac{C_p * (T_{mpre} - T_{lpre})}{H_{mflash} - H_{mpreliquid}} + \frac{C_p * (T_{lpre} - T_{room\,temperature})}{H_{lflash} - H_{lpreliquid}}$$

wherein, $M_{preheating}$ represents the quality of the steam that condenses into the pulp in pre-heating tower during steam heating in the unit time, and $H_{hflash}$, $H_{mflash}$, and $H_{lflash}$ respectively represents vapor enthalpies of the outlet temperatures of the high-temperature flash tank, the medium-temperature flash tank, and the low-temperature flash tank, and are obtained by combining the outlet temperatures of the high-temperature flash tank, the medium-temperature flash tank, and the low-temperature flash tank with database, $H_{hprliquid}$, $H_{mpreliquid}$, and $H_{lpreliquid}$ respectively represents liquid enthalpies of the outlet temperatures of the high-temperature preheating tower, the medium-temperature preheating tower, and the low-temperature preheating tower, and are obtained by combining the outlet temperatures of the high-temperature preheating tower, the medium-temperature preheating tower, and the low-temperature preheating tower with database, $T_{hpre}$, $T_{mpre}$, and $T_{lpre}$ respectively represents the outlet temperatures of the high-temperature preheating tower, the medium-temperature preheating tower, and the low-temperature preheating tower and $C_p$ represents a specific heat capacity of the pulp.

5. The system for optimizing duration time of high-pressure leaching of laterite nickel ore of claim 4, wherein the specific heat capacity of the pulp is calculated as follow:

$$C_p = 4.2 * (1 - c) + 0.364 * c$$

wherein $C_p$ represents the specific heat capacity of the pulp, c represents a solid content in the pulp, and is obtained by collecting a pulp flow rate and a pulp concentration.

6. The system for optimizing duration time of high-pressure leaching of laterite nickel ore of claim 3, wherein a specific calculation formula of obtaining a total feed quantity within the current unit time, according to the qualities of the pulp, the sulfuric acid, and the steam that enter the autoclave within the unit time, and the quality of steam that condenses into the pulp during steam heating in the preheating tower within the unit time is as follows:

$$M_{total} = M_{pulp} + M_{H_2SO_4} + M_{autoclave} + M_{preheating}$$

wherein, $M_{total}$ represents the total feed quantity within the current unit time, $M_{pulp}$, $M_{H_2SO_4}$, and $M_{autoclave}$ respectively represents the qualities of the pulp, the sulfuric acid, and the steam that enter the autoclave within the unit time during high-pressure leaching process, and $M_{preheating}$ represents the quality of the steam that condenses into the pulp in pre-heating tower during steam heating in the unit time.

7. The system for optimizing duration time of high-pressure leaching of laterite nickel ore of claim 2, wherein a specific calculation formula of obtaining a liquid density at the current leaching temperature, according to the leaching temperature in the autoclave is as follows:

$$\rho_T = 15.81747 + 9.87802 * T - 0.035239 T^2 + 5.38051 * 10^{-5} T^3 - 3.2612 * 10^{-8} T^4$$

wherein $\rho_T$ represents the liquid density at the current leaching temperature, and T represents the current leaching temperature.

8. The system for optimizing duration time of high-pressure leaching of laterite nickel ore of claim 2, wherein a specific calculation formula of obtaining the actual duration time of the pulp in the autoclave, according to the effective volume of the autoclave, the total feed amount in the unit time, and the liquid density at the current leaching temperature is as follows:

$$t_{act} = \frac{V}{W_T}$$

$$W_T = \frac{M_{total}}{\rho_T}$$

wherein, $t_{act}$ represents the actual duration time of the pulp in the autoclave, V represents the effective volume of the autoclave, $W_T$ represents a total feed flow rate, $M_{total}$ represents the total feed quantity within the current unit time, and $\rho_T$ represents the liquid density at the current leaching temperature.

9. The system for optimizing duration time of high-pressure leaching of laterite nickel ore of claim 1, wherein a specific method of the optimal duration time determining module configured to obtain an optimal duration time corresponding to a maximum income value, according to the qualities of the pulp, the sulfuric acid, and the steam that enter the autoclave within the unit time during the high-pressure leaching process, the outlet temperatures of the high-temperature preheating tower, the medium-temperature preheating tower, the low-temperature preheating tower, the high-temperature flash tank, the medium-temperature flash tank, the low-temperature flash tank, the leaching temperature in the autoclave, the composition of the pulp that enters the autoclave within the unit time, and the prices of nickel, sulfuric acid, and steam that enter the autoclave, comprises:
  setting different duration times in sequence;
  calculating each income value of each duration time; and
  comparing the income value at each duration time to obtain a duration time corresponding to the maximum income value as the optimal duration time, and outputting the optimal duration time.

10. The system for optimizing duration time of high-pressure leaching of laterite nickel ore of claim 9, wherein a specific calculation formula of calculating each income value of each duration time is as follows:

$$incomevalue = \left(M_{pulp} \times c_{Ni} \times X_{Ni} \times P_{Ni} - M_{H_2SO_4} P_{H_2SO_4} - M_{autoclave} P_{steam}\right) \times \frac{24\,h}{t}$$

$$3.12 \times 10^7 \times e^{-\frac{87.75 \times 10^3}{RT}} \frac{M_{H_2SO_4}}{W_T} t = 1 - 3(1 - X_{Ni})^{\frac{2}{3}} + 2(1 - X_{Ni})$$

wherein, $P_{Ni}$, $P_{H_2SO_4}$, and steam, respectively represent the prices of metal nickel, sulfuric acid, and steam in the unit mass, Ni represents a content of Ni in the pulp, $M_{pulp}$, $M_{H_2SO_4}$, and $M_{autoclave}$ respectively represent the qualities of the pulp, the sulfuric acid, and the steam that enter the autoclave within the unit time during the high-pressure leaching process, $X_{Ni}$ represents a conversion rate of Ni in the pulp, represents an hour, T represents the current leaching temperature, $M_{H_2SO_4}$ represents a quality of sulfuric acid entering the autoclave in the unit time during the high-pressure leaching process, $W_T$ represents a total feed flow rate, t represents the current set duration time, and R represents a gas constant.

11. The system for optimizing duration time of high-pressure leaching of laterite nickel ore of claim 1, wherein a specific method of the duration time control module configured to compare an actual duration time with the optimal duration time under this condition, and control opening degrees of a feed valve and a discharge valve of the autoclave by using a feedback control system, to ensure the actual duration time of the pulp in the autoclave is within the optimal duration time all the time, comprises:
  if the current actual duration time is less than the optimal duration time, reduce the opening of the feed valve and/or the discharge valve of the autoclave; and
  if the current actual duration time is greater than the optimal duration time, increase the opening of the feed valve and/or the discharge valve of the high-pressure.

\* \* \* \* \*